United States Patent [19]

Montgomery

[11] Patent Number: 5,310,541
[45] Date of Patent: May 10, 1994

[54] ANTIMICROBIAL RAWHIDE ANIMAL CHEW CONTAINING AN OXIDOREDUCTASE AND OXIDOREDUCTASE SUBSTRATE

[76] Inventor: Robert E. Montgomery, 8916 Hollywood Hills Rd., Los Angeles, Calif. 90046

[21] Appl. No.: 936,929

[22] Filed: Aug. 27, 1992

[51] Int. Cl.$^5$ .................. A61K 7/28; A61K 37/50
[52] U.S. Cl. ................................ 424/50; 424/94.4
[58] Field of Search ................ 424/48, 49, 50, 57, 424/438, 439, 94.4

[56] References Cited

U.S. PATENT DOCUMENTS

| | | | |
|---|---|---|---|
| 4,476,108 | 10/1984 | Kessler et al. | 424/94.4 |
| 4,537,764 | 8/1985 | Pellico et al. | 424/50 |
| 4,564,519 | 1/1986 | Pellico et al. | 424/50 |
| 4,578,265 | 3/1986 | Pellico et al. | 424/50 |
| 5,011,679 | 4/1991 | Spanier et al. | 424/57 |
| 5,114,704 | 5/1992 | Spanier et al. | 424/57 |

Primary Examiner—Douglas W. Robinson
Assistant Examiner—Jeffrey J. Sevigny
Attorney, Agent, or Firm—Blakely, Sokoloff, Taylor, Zafman

[57] ABSTRACT

The invention is an animal chew which contains one or more enzymes and substrates for the purpose of generating antimicrobial compounds upon contact with an animal's saliva. The animal chew, primarily made of rawhide, contains an oxidoreductase and substrate, such as, for example, glucose oxidase and glucose, which produces hydrogen peroxide upon being chewed. The hydrogen peroxide activates the salivary peroxide system present in the saliva, which in turn produces hypothiocyanite, a potent antimicrobial agent. The animal chew may also contain added thiocyanate and iodide ions to enhance its antimicrobial activity. The chew is preferably prepared by placing it into a substrate solution for a period, drying the chew, spraying the dried rawhide chew with a solution of the oxidoreductase, and finally drying the chew again.

20 Claims, No Drawings

ANTIMICROBIAL RAWHIDE ANIMAL CHEW CONTAINING AN OXIDOREDUCTASE AND OXIDOREDUCTASE SUBSTRATE

BACKGROUND OF THE INVENTION

1. Field of the Invention

This invention relates to a chewable object for animals which contains one or more enzymes and substrates for the purpose of generating antimicrobial compounds upon contact with an animal's saliva. More specifically, chewable and consumable compositions are herein described which, upon being chewed, produce hydrogen peroxide or other antimicrobial agents.

2. Art Background

A number of naturally occurring antimicrobial systems rely upon the ability of certain oxidizing agents to disrupt metabolic processes of bacteria, fungi and viruses. Compounds such as hypothiocyanite (OSCN-/HOSCN), hypochlorite (OCI-, HOCl), and hypoiodite (OI-, HOI) are known to inhibit glycolysis, penetrate prokaryotic cell walls, and generally disrupt a wide variety of processes crucial to the survival of lower organisms. These oxidizing agents are the result of the detoxification of hydrogen peroxide by mammalian peroxidase systems, such as those found in saliva, cervical fluid, lacrimal fluid, and leukocytes.

The antimicrobial effectiveness of the aforementioned oxidizing agents is well established in the literature and is known to occur at concentrations of about 100 micromoles per liter. The limiting factor in all of the mammalian antimicrobial peroxidase systems is the availability of hydrogen peroxide.

The numerous prior art attempts to activate or supplement natural antimicrobial peroxidase systems are generally limited to the oral care field. U.S. Pat. No. 4,150,113 and U.S. Pat. No. 4,178,362 (Hoogendorn, et al) describe dentifrices containing glucose oxidase in order to react with plaque and salivary glucose to produce low levels of hydrogen peroxide.

U.S. Pat. Nos. 4,269,822, 4,564,519 and 4,578,265 (Pellico, et al.) further describe dentifrice compositions containing an oxidoreductase enzyme, together with its specific substrate, for the purpose of producing hydrogen peroxide or other antimicrobial oxidizing compounds, such as hypothiocyanite ion. In each of these prior art formulations, the oxidoreductase enzymes and substrates are in aqueous solution and homogeneously distributed throughout the entire mixture.

U.S. Pat. No. 4,564,519 describes a chewable dentifrice, such as a chewing gum or lozenge, which contains a dual enzyme system for producing hypothiocyanite ions upon being chewed or otherwise activated by the moisture in saliva. All of the above compositions teach a manufacturing and compounding process whereby the enzymes, and, optionally, the substrates are distributed homogeneously throughout the entire composition.

In addition to U.S. Pat. No. 4,564,519 above, other solid or chewable compositions capable of producing hydrogen peroxide or other oxidizing agents upon activation with moisture are taught in U.S. Pat. Nos. 4,320,116, 4,726,948, and 4,929,466. These compositions are foodstuffs intended for consumption by livestock in order to limit the growth of harmful bacterial within the animal's gastrointestinal tract. The authors also teach a manufacturing and compounding process whereby the enzymes and substrates are distributed homogeneously throughout the composition.

It is well known to those skilled in the art that enzymes are reactive with their corresponding substrates when present together in aqueous solution. It is also well known by those skilled in the art that most enzymes are thermosensitive and frequently undergo a gradual, but irreversible inhibition when exposed to temperatures higher than 5 or 10 degrees Celsius for extended periods of time.

Since domesticated animals, such as dogs, are unable to practice any type of oral hygiene, they are more at risk for caries, gingivitis and periodontal disease than their human counterparts. It would thus be advantageous to provide a chewable and consumable object for animals which contains or can produce agents effective in reducing or eliminating oral pathogens associated with such diseases.

SUMMARY OF THE INVENTION

The present invention provides a chewable and consumable composition which is capable of producing one or more antimicrobial agents upon contact with saliva, for the purpose of reducing, normalizing, or otherwise eliminating potentially harmful oral pathogens in the oral cavity of domesticated animals. More particularly, compositions are herein described which, upon being chewed, release an oxidoreductase enzyme, together with its corresponding substrate, into salivary solution in an animal's mouth, wherein the ensuing enzymatic reaction proceeds and produces hydrogen peroxide. The hydrogen peroxide thus produced is capable of activating the salivary peroxidase system already present in saliva, which in turn produces the potent antimicrobial species known as hypothiocyanite ion (OSCN-/HOSCN). The aforementioned compositions should be of a durable enough construction so that the residence, or chewing, time in an animal's mouth is of sufficient duration to allow the production or accumulation of a hydrogen peroxide concentration capable of raising salivary hypothiocyanite levels to at least about 100 micromoles per liter of salivary fluid.

Once in salivary solution, the general reaction which ensues is as follows:

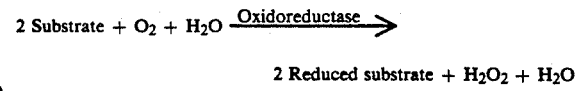

$$2 \text{ Substrate} + O_2 + H_2O \xrightarrow{\text{Oxidoreductase}} 2 \text{ Reduced substrate} + H_2O_2 + H_2O$$

The hydrogen peroxide produced in salivary solution as a result of the above reaction scheme is a further participant in the following sequence:

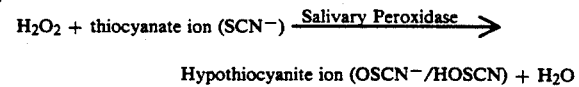

$$H_2O_2 + \text{thiocyanate ion (SCN}^-) \xrightarrow{\text{Salivary Peroxidase}} \text{Hypothiocyanite ion (OSCN}^-/\text{HOSCN)} + H_2O$$

The hypothiocyanite ion (OSCN-) exists in equilibrium with hypothiocyanous acid (HOSCN) while in solution, and the distribution of the two species is dependent upon pH. The pKa of hypothiocyanous acid (HOSCN) is 5.3. Thus the preferred pH of the present invention is in the range of 5.5–7.0.

The elevated levels of hypothiocyanite (OSCN-/HOSCN) thus produced inhibits oral pathogens, as heretofore described.

DETAILED DESCRIPTION OF THE INVENTION

In its simplest form, the antimicrobial animal chew of the present invention comprises a solid, chewable composition or material on or in which an oxidoreductase enzyme and its corresponding substrate have been applied or otherwise deposited. When in contact with an animal's saliva during the process of chewing, the oxidoreductase enzyme and its corresponding substrate are solubilized into aqueous solution, whence they react as previously described to produce hydrogen peroxide. The hydrogen peroxide produced is then utilized by salivary peroxidase to further oxidize thiocyanate ions (SCN-) to antimicrobial hypothiocyanite ions (OSCN-/HOSCN).

The carrier is herein defined as the portion of the animal chew which is intended for the dog or other animal to chew on. The preferred carrier material of the present is rawhide; however any material which is safely consumable and durable enough to satisfy the certain chewing or oral residence time requirements is contemplated.

The solid, chewable carrier is preferably durable enough to prevent the animal from consuming it in less than about 1 to 5 minutes. This length of time is sufficient to allow the production of antimicrobial concentrations of hypothiocyanite ions, generally at a level of about 100 micromoles per liter of salivary fluid.

Suitable oxidoreductases include, but are not limited to, glucose oxidase, galactose oxidase, glycollate oxidase, lactate oxidase, L-gulunolactone oxidase, L-2-hydroxyacid oxidase, aldehyde oxidase, xanthine oxidase, D-aspartate oxidase, L-amino acid oxidase, D-amino acid oxidase, monoamine oxidase, pyridoxaminephosphate oxidase, diamine oxidase, and sulfite oxidase. The preferred oxidoreductase is glucose oxidase.

Suitable substrates are specific to the particular oxidoreductase chosen and are well known in the art. For instance, D-glucose is a specific substrate for glucose oxidase. Other suitable substrates include, but are not limited to D-glucose, D-galactose, L-sorbose, ethanol, tyramine, 1, 4-diaminobutane, 6-hydroxy-L-nicotine, 6-hydroxy-D-nicotine, 2-aminophenol, glycollate, L-lactate, 2-deoxy-D-Glucose, L-gulunolactone, L-galactonolactone, D-mannonolactone, L-2-hydroxyisocaproate, acetaldehyde, butyraldehyde, xanthine, D-aspartate, D-glutamate, L-amino acids and D-amino acids.

The antimicrobial animal chew of this invention comprises at least one of the above listed oxidoreductase enzymes together with its corresponding substrate, also listed above. For the purpose of this invention, a specific amount or activity of oxidoreductase enzyme shall be described in Titrimetric Units (TU), which is that amount of oxidoreductase enzyme capable of producing 1.1 micromole of hydrogen peroxide per minute at 35° C., and optimal conditions of pH and substrate concentration for each particular oxidoreductase enzyme.

In general, the antimicrobial animal chews should contain at least about 1.0 TU of oxidoreductase enzyme per gram of carrier. A preferable level of oxidoreductase enzyme activity is from 5.0 to 50 TU per gram of carrier.

The corresponding substrate should be present in or on the antimicrobial animal chew at a level of at least 0.1 percent by weight of the total carrier weight (0.001 grams of substrate per gram of carrier). A preferable level of substrate is from 0.5 to 10 percent by weight of the total carrier weight.

The antimicrobial animal chew may optionally contain or carry stabilizers, buffers, cofactors, and/or activators for the aforementioned oxidoreductase enzymes. Such optional components are intended to stabilize the activity and/or prevent denaturation of the oxidoreductase enzyme during the manufacture and storage of the inventive animal chew, and are well known in the art. Any such optional components must be biologically acceptable and suitable for ingestion by the animal. In addition, the suitability and function of an optional component as described herein is dependent upon the particular oxidoreductase enzyme present.

In general, suitable optional components include polymeric stabilizers such as gelatin, albumin, and casein. Suitable buffering components include potassium phosphate monobasic, potassium phosphate dibasic, sodium phosphate monobasic, and sodium phosphate dibasic, and may be employed to adjust the animal's salivary pH to that which is optimal for the particular oxidoreductase enzyme selected. A suitable cofactor or activator (for glucose oxidase) is flavin adenine dinucleotide (FAD). Any optional component which can contribute to the preservation or potentiation of a particular oxidoreductase enzyme's activity within the parameters of its use on an antimicrobial animal chew is contemplated to be within the scope of this invention.

In addition to the above, the inventive animal chew may contain one or more peroxidase enzymes for the purpose of assuring the optimal utilization of the hydrogen peroxide produced by the oxidoreductase enzyme and its corresponding substrate. Suitable peroxidase enzymes include, but are not limited to, lactoperoxidase and salivary peroxidase. Any peroxidase capable of utilizing hydrogen peroxide to oxidize thiocyanate ions to form hypothiocyanite ions is contemplated. The preferred peroxidase is lactoperoxidase.

Peroxidase activity is measured, for the purpose of this invention, in ABTS Units. One ABTS Unit is the amount of peroxidase capable of oxidizing one micromole of ABTS (2,2'-azinobis(3-ethylbenzothiazoline-6-sulfonic acid)) per minute at 25° C., 0.1M phosphate buffer (pH 6.0), and initial hydrogen peroxide concentration of 1.0 mM.

In general, the antimicrobial animal chew may optionally contain or carry any level of peroxidase within economic practicality, however a preferred level is from 10.0 to 100 ABTS Units of peroxidase per gram of carrier.

The compositions of the present invention may also include a thiocyanate ion source such as potassium thiocyanate, sodium thiocyanate, ammonium thiocyanate, or other thiocyanate salts in order to optimize the final concentration of thiocyanate in the animal's saliva during the chewing cycle. The preferred thiocyanate ion source is potassium thiocyanate. Since salivary peroxidase is also capable of oxidizing iodide ions (I-) to antimicrobial hypoiodite ions (OI-/HOI), an iodide ion source such as potassium iodide may be included to enhance the chew's antimicrobial activity.

Additional optional ingredients include flavorants and colorants, which are related to the organoleptic properties of the animal chew, and are well known in the art.

EXAMPLE I

Commercially available rectangular rawhide chews of a dimension approximately 2" wide and 4" in length were individually weighed and then placed in a 15% (w/w) aqueous solution of dextrose (D-glucose) for a period of 120 minutes, then removed and placed in a constant temperature oven set at 45° C. to dry for 24 hours. After drying, the weight gain attributable to D-glucose deposition on the rawhide chew averaged 2.2 mg per gram of chew. The dry, D-glucose-impregnated chews were then contacted on one side only with a metered spray of a glucose oxidase solution (Code F100, Genencor Inc., Rochester, N.Y., diluted with distilled water to yield an activity of 100 TU per ml of solution), and dried in a constant temperature oven at 45° C. for 2 hours. The final activity of the dried chews was calculated to be 9.5 TU per gram of chew, based on the volume of glucose oxidase solution applied prior to drying. The chews were then assayed for hydrogen peroxide production as outlined below.

In Vitro Hydrogen Peroxide Determination of Rawhide Animal Chew

This procedure is based on the ability of a rawhide chew containing an oxidoreductase enzyme and its substrate (glucose oxidase and glucose, respectively) to produce hydrogen peroxide upon being chewed by the animal. The water provided by saliva activates the enzyme/substrate combination, producing detectable levels of hydrogen peroxide.

A representative volume of water was chosen based upon the assumption that a single chew, with an average weight of 10 grams would come in contact with approximately 15 milliliters or grams of water from the animal's saliva. Thus, 1.0 grams of rawhide chew is combined with 1.5 milliliter of water (or any other multiple of this ratio) in the testing procedure.

The detection of hydrogen peroxide in the "chew fluid" is based upon the procedure developed by Mottola, et al., Analytical Chemistry, Vol. 42, No. 3, March 1970, pgs 410–11.

Solutions (a) 50 mg of Leucocrystal violet (LCV, Sigma Chemical Co., St. Louis, Mo.) was dissolved in about 80 ml of 0.5% (v/v) hydrochloric acid and diluted to 100 ml with acid of the same strength.

(b) The buffer was made by mixing equal volumes of 2M sodium acetate and 2M acetic acid, then adjusting the pH to 4.5 with glacial acetic acid.

(d) A solution of horseradish peroxidase (HRP, Sigma Chemical Co., St. Louis, Mo.) was prepared as needed by dissolving 10 mg of the lyophilized enzyme in 10 ml of distilled water.

All solutions, except the buffer, should be refrigerated during storage.

Procedure

Note: An untreated rawhide chew should always be run as a control.

(a) The rawhide chew to be assayed is sliced into small squares, approximately ¼ inch on a side, with large, durable scissors. 6.0 grams of rawhide chew squares are weighed and transferred to a 20 ml plastic scintillation vial with screw cap.

(b) 9.0 ml of distilled water is added to the vial, which is then vortexed for a period of five minutes, during which time 50 microliter samples of "chew fluid" will be drawn at regular intervals (one minute, three minutes and five minutes).

(c) Each 50 microliter aliquot is immediately transferred to a 10 ml volumetric flask, to which 1.0 ml of LCV solution is then added.

(d) 0.5 ml of HRP solution is added to the flask, followed by 4.0 ml of buffer, and the mixture diluted to 10 ml with distilled water.

(e) Absorbance of the sample is read at 596 nm against a reference prepared in the same manner, however using 50 microliters of distilled water instead of "chew fluid".

Calculations $$\text{Absorbance}_{596} = \frac{\text{Molar extinction coefficient } (LCV) \times [H_2O_2]}{\text{Dilution factor}}$$

$$\text{Absorbance}_{596} = \frac{75{,}000 \, M^{-1} \, cm^{-1} \times [H_2O_2]}{200}$$

$[\text{Hydrogen peroxide in chew fluid}] = \text{Absorbance}_{596} \times 0.002667$ An increase in absorbance of 1.00 at 596 nm is equivalent to a hydrogen peroxide concentration of 2.667 millimoles per liter of "chew fluid".

Twelve chews were assayed according to the procedure outlined above. The average concentrations of hydrogen peroxide generated by the inventive chews was as follows:

| $[H_2O_2]^1$ | $[H_2O_2]^2$ | $[H_2O_2]^3$ |
|---|---|---|
| 0.534 mM | 1.227 mM | 1.585 mM |

[1] Average concentration of hydrogen peroxide in chew fluid at one minute.
[2] Average concentration of hydrogen peroxide in chew fluid at three minutes.
[3] Average concentration of hydrogen peroxide in chew fluid at five minutes.

In addition to the process for manufacturing the antimicrobial animal chew of the present invention delineated in Example I, other methods of applying an oxidoreductase enzyme and its corresponding substrate are contemplated. For example, in order to avoid the additional drying step at elevated temperature, a chew may be manufactured by contacting its surface with a granulated or otherwise solid mixture of oxidoreductase enzyme, substrate, and heretofore described optional components, in addition to granulating agents or carriers such as starch or proteinaceous material such as gelatin, casein and albumin. Such a granulated mixture adheres to a slightly moistened chew surface without dissolving, thus avoiding a premature reaction between the oxidoreductase enzyme and its corresponding substrate to ensue.

The foregoing description of the invention is intended to be exemplary with respect to certain preferred embodiments and it will be understood that modifications and variations thereof obvious to those skilled in the art are to be included within the scope of this application and the appended claims.

I claim:

1. An antimicrobial animal chew comprising a rawhide chewable carrier material, at least one oxidoreductase and at least one oxidoreductase substrate, said animal chew being made by the process comprising:

a) providing a rawhide animal chew:
b) applying said substrate to said animal chew by absorbing said substrate in liquid form into said animal chew and drying the substrate therein and thereon; and
c) thereafter coating said oxidoreductase on the outside of said animal chew and drying the coating thereon.

2. The animal chew of claim 1 wherein said oxidoreductase is selected from the group consisting of glucose oxidase, galactose oxidase, glycollate oxidase, lactate oxidase, L-gulunolactone oxidase, L-2-hydroxyacid oxidase, aldehyde oxidase, xanthine oxidase, D-aspartate oxidase, L-amino acid oxidase, D-amino acid oxidase, monoamine oxidase, pyridoxaminephosphate oxidase, diamine oxidase, and sulfite oxidase.

3. The animal chew of claim 1 wherein said oxidoreductase is glucose oxidase.

4. The animal chew of claim 1 wherein said substrate is selected from the group consisting of D-glucose, D-galactose, L-sorbose, ethanol, tyramine, 1,4-diaminobutane, 6-hydroxy-L-nicotine, 6-hydroxy-D-nicotine, 2-aminophenol, glycollate, L-lactate, 2-deoxy-D-Glucose, L-gulunolactone, L-galactonolactone, D-mannonolactone, L-2-hydroxyisocaproate, acetaldehyde, butyraldehyde, xanthine, D-aspartate, D-glutamate, L-amino acids and D-amino acids.

5. The animal chew of claim 1 wherein said oxidoreductase is glucose oxidase and said substrate is D-glucose.

6. The animal chew of claim 1 further comprising a peroxidase.

7. The animal chew of claim 6 wherein the peroxidase is selected from the group consisting lactoperoxidase and salivary peroxidase.

8. The animal chew of claim 7 wherein the peroxidase is lactoperoxidase.

9. The animal chew of claim 1 wherein said oxidoreductase is present at a level of at least about 1.0 TU of oxidoreductase per gram of carrier material.

10. The animal chew of claim 9 wherein the level of oxidoreductase activity is in the range of 5.0 to 50 TU per gram of carrier.

11. The animal chew of claim 1 wherein said substrate is present in or on the antimicrobial animal chew at a level of at least 0.1 percent by weight of the carrier material.

12. The animal chew of claim 11 wherein said substrate level is in the range from 0.5 to 10 percent by weight of the carrier material.

13. The animal chew of claim 6 wherein said peroxidase is present in the range of from 10.0 to 100 ABTS Units of peroxidase per gram of carrier.

14. The animal chew of claim 1 wherein said substrate comprises an aqueous solution of dextrose which applies approximately 2.2 mg of dextrose per gram of chew.

15. The animal chew of claim 1 wherein said chew is dried in step b at 45° C. for 24 hours.

16. The animal chew of claim 1 wherein said oxidoreductase is applied by contacting said chew with a glucose oxidase solution.

17. The animal chew of claim 16 wherein said oxidoreductase is sprayed on said chew.

18. The animal chew of claim 16 wherein said oxidoreductase is in an aqueous solution containing an enzyme activity of 100 TU per ml of solution.

19. The animal chew of claim 16 wherein said oxidoreductase comprises an aqueous solution of glucose oxidase which applies approximately 9.5 TU of glucose oxidase per gram of chew.

20. The animal chew of claim 1 wherein the drying step of step c is carried out at 45° C. for 2 hours.

* * * * *